US006444874B1

United States Patent
Duvick et al.

(10) Patent No.: US 6,444,874 B1
(45) Date of Patent: Sep. 3, 2002

(54) HYDROPEROXIDE LYASE GENE FROM MAIZE AND METHODS OF USE

(75) Inventors: Jon Duvick, Des Moines; Jacob Gilliam, Norwalk, both of IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/417,704

(22) Filed: Oct. 13, 1999

Related U.S. Application Data

(60) Provisional application No. 60/104,084, filed on Oct. 13, 1998.

(51) Int. Cl.$^7$ .............................. A01H 5/00; A01H 5/10; C12N 5/04; C12N 15/29; C12N 15/60; C12N 15/82

(52) U.S. Cl. ..................... 800/278; 80/320.3; 80/320.2; 80/320.1; 80/320; 80/312; 80/322; 80/317.1; 80/306; 80/279; 80/287; 80/281; 536/232; 536/236; 435/418; 435/419; 435/412; 435/415; 435/416; 435/468

(58) Field of Search ............................... 536/23.2, 23.6; 800/279, 320, 320.1, 320.3, 320.2, 301, 312, 322, 317.1, 287, 281, 306, 278; 435/418, 419, 412, 415, 416, 468

(56) References Cited

U.S. PATENT DOCUMENTS

| | | | | |
|---|---|---|---|---|
| 5,728,925 A | * | 3/1998 | Herrera-Estrella et al. | .. 800/205 |
| 6,008,034 A | * | 12/1999 | Hausler et al. | ............. 435/232 |
| 6,200,794 B1 | * | 3/2001 | Whitehead et al. | ......... 435/232 |

FOREIGN PATENT DOCUMENTS

| | | |
|---|---|---|
| EP | 0 801 133 A2 | 10/1997 |
| WO | WO 97/26364 | 7/1997 |
| WO | WO 99/58648 | 11/1999 |
| WO | WO 00/00627 | 1/2000 |

OTHER PUBLICATIONS

Hause, B. et al., "A Jasmonate–responsive Lipoxygenase of Barley Leaves is Induced by Plant Activators but not by Pathogens." 1999, J. Plant Physiol., vol. 154, pp. 459–462.*

Chee, P.P. et al., "Transformation of Soybean (Glycine max) by Infecting Germinating Seeds with Agrobacterium tumefaciens." 1989, Plant Physiol., vol. 91, pp. 1212–1218.*

Gordon–Kamm, W. J. et al., "Transformation of Maize Cells and Regeneration of Fertile transgenic Plants." 1990, The Plant Cell. vol. 2, pp. 603–618.*

Datla, R. et al., "Plant promoters for transgene expression." 1997, Biotechnol. Ann. Rev., vol. 3, pp. 269–296.*

Matsui, K. et al., "Molecular Cloning and Expression of Arabidopsis Fatty Acid Hdroperoxide Lyase." 1999, Plant Cell Physiol., vol. 40, pp. 477–481.*

Lazar, E. et al., "Transforming Growth Factor a: Mutation of Aspartic Acid 47 and Leucine 48 Results in Different Biological Activities." 1988, Molecular and Cellular Biology, vol. 8, pp. 1247–1252.*

Broun, P. et al., "Catalytic Plasticity of Fatty Acid Modification Enzymes Underlying Chemical Diversity of Plant Lipids." 1998, Science, vol. 282, pp. 1315–1317.*

Hill, M. A. and Preiss, J., "Functional Analysis of Conserved Histidines in ADP–Glucose Pyrophosphorylase from *Escherichia coli.*" 1998, Biochemical and Biophysical Res. Co,,., vol. 244, pp. 573–577.*

Song, W. C. et al., Accession No. U00428, Proc. Natl. Acad. Sci, 1993.*

Maucher, H. et al., Accession No. AJ250864, Plant J., 2000.* maucher, H. et al., Accession No. AJ251304, Plant J., 2000.*

Matsui, K., Accession No. A64011, Aug. 31, 2000.*

Matsui, K. Accession No. Z49781, Jan. 6, 2000.*

Matsui, K., Accession No. A64010, Aug. 31, 2000.*

Backhaus, R., Patent No. 5633433.*

Ashley, G., Patent No. 6117659.*

Bate, N.J., Molecular Characterization of an Arabidopsis Gene Encoding Hydroperoxide Lyase, a Cytochrome P–450 That is Wound Inducible, Plant Physiol., 1998, vol. 117, pp. 1393–1400.

Larkin, J.C., Isolation of a Cytochrome P450 Homologue Preferentially Expressed in Developing Inflorescenes of Zea Mays, Plant Molecular Biology, 1994, vol. 25, pp. 343–353.

Matsui, K., Properties and Structures of Fatty Acid Hydroperoxide Lyase, Belg. Journ. Bot., 1998, vol. 131(1), pp. 50–62.

Bisakowski B., et al., Charcterization of Hydroperoxides and Carbonyl Compounds Obtained by Lipoxygenase Extracts of Selected Microorganisms, Biosci. Biotech. Biochem., 1997, vol. 61, No. 8, pp. 1262–1269.

Blée E., et al., Envelope Membranes From Spinach Chloroplasts Are a Site of Metabolism of Fatty Acid Hydroperoxides, Plant Physiol., 1996, vol. 110, pp. 445–454.

Gardner H., et al., Hexanal, trans–2–Hexenal, and trans–2 Nonenal Inhibit Soybean, Glycine max, Seed Germination, J. Argic. Food Chem., 1990, vol. 38, pp. 1316–1320.

(List continued on next page.)

*Primary Examiner*—David T. Fox
*Assistant Examiner*—Anne Kubelik
(74) *Attorney, Agent, or Firm*—Alston & Bird LLP

(57) ABSTRACT

Compositions and methods for enhancing disease resistance, and modulating levels of flavor molecules in plants are provided. The compositions comprise nucleotide sequences encoding maize HPL genes. The methods comprise expressing hydroperoxide lyase (HPL) genes in plants, plant cells, and plant tissues. Expression cassettes comprising the HPL sequences of the invention are provided, as well as transformed plant cells, plant tissues, and plants.

17 Claims, 3 Drawing Sheets

OTHER PUBLICATIONS

Gardner H., Sequential Enzymes of Linoleic Acid Oxidation in Corn Germ: Lipoxygenase and Linoleate Hydroperoxide Isomerase, Journal of Lipid Research, 1970, vol. 11, pp. 311–321.

Götz–Schmidt E., et al., $C_6$–Volatiles in Homogenates from Green Leaves: Localization of Hydroperoxide Lyase Activity, 1986, Lebensm.–Wiss. U Technol., vol. 19, pp. 152–155.

Gueldner R., et al., Volatile Compounds Inhibiting Aspergillus Flavus, 1985, The American Chemical Society, vol. 33, pp. 411–413.

Hatanaka A., et al., Fatty Acid Hydroperoxide Lyase in Plant Tissues, American Chemical Society, 1986, pp. 166–175.

Matsuik., et al., Bell Pepper Fruit Fatty Acid Hydroperoxide Lyase is a Cytochrome P450 (CYP74B), FEBS Letters, 1996, vol. 394, pp. 21–24.

Sekiya J., et al., Distribution of Lipoxygenase and Hydroperoxide Lyase in the Leaves of Various Plant Species, Phytochemistry, 1983, vol. 22, No. 9, pp. 1867–1869.

Sekiya J., et al., Fatty Acid Hydroperoxide Lyase in Tobocco Cells Cultured in vitro, Phytochemistry, 1984, vol. 23, No. 11, pp. 2439–2443.

Shibata Y., Purification and Properties of Fatty Acid Hydroperoxide Lyase from Green Bell Pepper Fruits, 1995, Plant Cell Physiol. vol. 36, No. 1, pp. 147–156.

Vaughn S., et al., Lipoxygenase–Derived Aldehydes Inhibit Fungi Pathogenic on Soybean, Journal of Chemical Ecology, 1993, vol. 19, No. 10, pp. 2337–2345.

Vick B., A Spectrophotometric Assay for Hydroperoxide Lyase, LIPIDS, 1991, vol. 26, No. 4, pp. 315–320.

Zeringue H., Relationship between $C_6$–$C_{12}$ Alkanal and Alkenal Volatile Contents and Resistance of Maize Genotypes to Aspergillus Flavus and Aflatoxin Production, J. Agric. Food Chem., 1996, vol. 44, pp. 403–407.

Doehlert, et al., Abstract, Evidence Implicating the Lipoxygenase Pathway in Proiding Resistance to Soybeans against Aspergillus Flavus, American Phytophathological Society, 1993, vol. 83, No. 12, pp. 1473–1477.

* cited by examiner

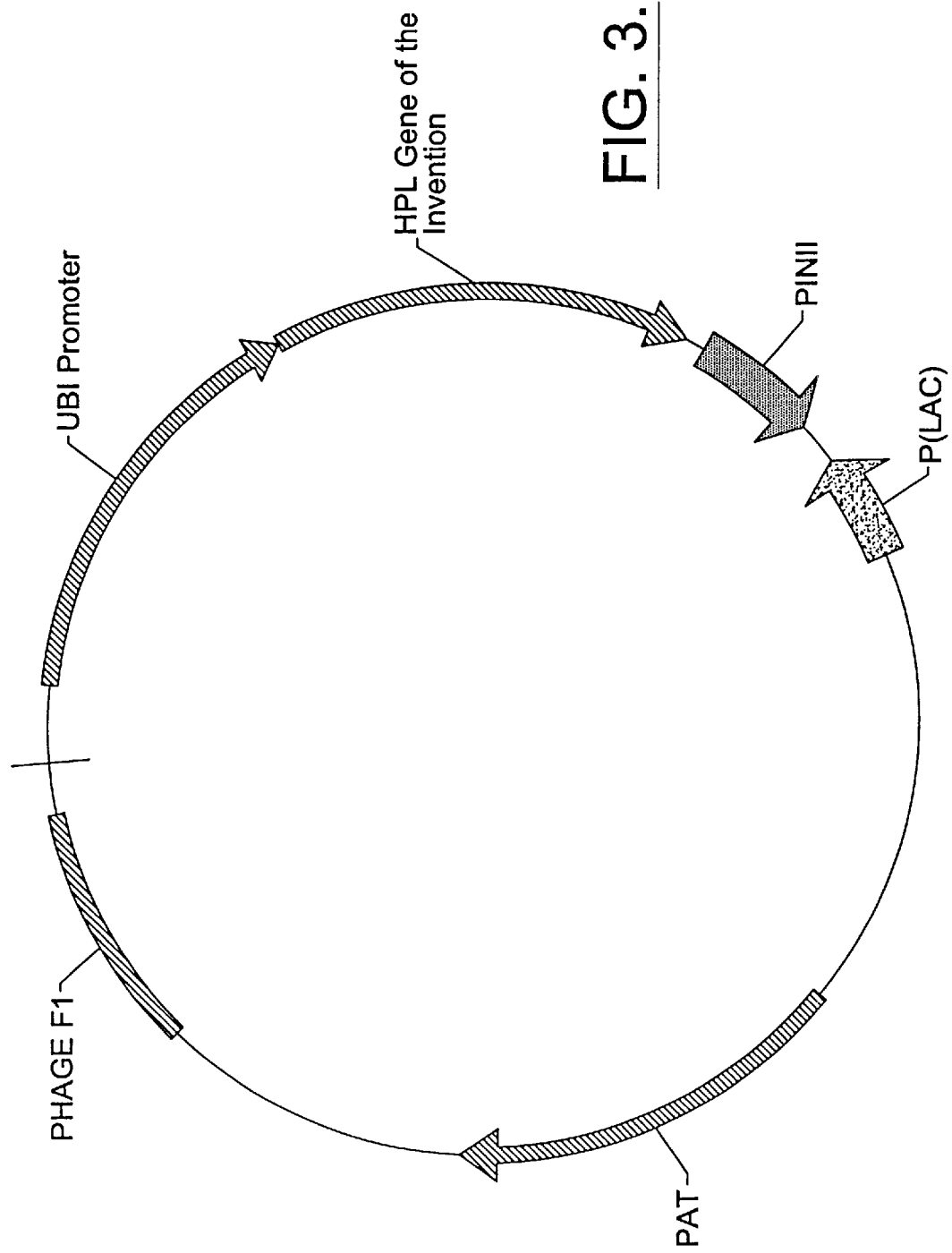

SEQUENCE LISTING

```
<160> NUMBER OF SEQ ID NOS: 2

<210> SEQ ID NO 1
<211> LENGTH: 502
<212> TYPE: PRT
<213> ORGANISM: Zea mays
<220> FEATURE:
<221> NAME/KEY: HELIX
<222> LOCATION: (304)
<223> OTHER INFORMATION: I-helix: Forms Oxygen binding pocket
<220> FEATURE:
<223> OTHER INFORMATION: (356)..(359) Highly-conserved in P450's (ETLR)
<220> FEATURE:
<223> OTHER INFORMATION: (402)..(413) Highly-conserved in P450's (KDP
      XXXX PEEF)
<220> FEATURE:
<221> NAME/KEY: BINDING
<222> LOCATION: (448)
<223> OTHER INFORMATION: Heme-binding site

<400> SEQUENCE: 1

Met Leu Pro Ser Phe Val Ser Pro Thr Ala Ser Ala Ala Ala Ser Val
  1               5                  10                  15

Thr Pro Pro Pro Arg Pro Ile Pro Gly Ser Tyr Gly Pro Pro Val Leu
                 20                  25                  30

Gly Pro Leu Arg Asp Arg Leu Asp Tyr Phe Trp Phe Gln Ser Gln Asp
             35                  40                  45

Glu Phe Phe Arg Lys Arg Ala Ala Ala His Arg Ser Thr Val Phe Arg
         50                  55                  60

Thr Asn Ile Pro Pro Thr Phe Pro Phe Phe Val Gly Val Asp Pro Arg
 65                  70                  75                  80

Val Val Ala Ile Val Asp Ala Ala Ala Phe Thr Ala Leu Phe Asp Pro
                     85                  90                  95

Asp Leu Val Asp Lys Arg Asp Ile Leu Ile Gly Pro Tyr Asn Pro Gly
                100                 105                 110
```

```
Ala Gly Phe Thr Gly Gly Thr Arg Val Gly Val Tyr Leu Asp Thr Gln
            115                 120                 125

Glu Glu Glu His Ala Arg Val Lys Thr Phe Ala Met Asp Leu Leu His
130                 135                 140

Arg Ser Ala Arg Thr Trp Ser Ala Asp Phe Arg Ala Ser Val Gly Ala
145                 150                 155                 160

Met Leu Asp Ala Val Asp Ala Glu Phe Gly Lys Asp Asp Gly Ser Asp
            165                 170                 175

Lys Lys Pro Ser Ala Ser Tyr Leu Val Pro Leu Gln Gln Cys Ile Phe
            180                 185                 190

Arg Phe Leu Cys Lys Ala Phe Val Gly Ala Asp Pro Ser Ala Asp Trp
            195                 200                 205

Leu Val Asp Asn Phe Gly Phe Thr Ile Leu Asp Ile Trp Leu Ala Leu
210                 215                 220

Gln Ile Leu Pro Thr Gln Lys Ile Gly Leu Val Gln Pro Leu Glu Glu
225                 230                 235                 240

Leu Leu Ile His Ser Phe Pro Leu Pro Ser Phe Leu Ile Trp Pro Gly
            245                 250                 255

Tyr Tyr Val Leu Tyr Arg Phe Ile Glu Lys His Gly Ala Glu Ala Val
            260                 265                 270

Ala Tyr Ala Glu Ala Gln His Gly Ile Gly Lys Lys Asp Ala Ile Asn
            275                 280                 285

Asn Ile Leu Phe Val Leu Gly Phe Asn Ala Phe Gly Gly Phe Ser Val
            290                 295                 300

Phe Leu Pro Phe Leu Val Ala Lys Val Gly Gly Ala Pro Ala Leu Arg
305                 310                 315                 320

Glu Arg Leu Arg Asp Glu Val Arg Arg Ala Met Val Gly Lys Asp Gly
                325                 330                 335

Glu Phe Gly Phe Ala Thr Val Arg Glu Gly Met Pro Leu Val Arg Ser
            340                 345                 350

Thr Val Tyr Glu Met Leu Arg Met Gln Pro Pro Val Pro Leu Gln Phe
            355                 360                 365

Gly Arg Ala Arg Arg Asp Phe Val Leu Arg Ser His Gly Gly Ala Ala
370                 375                 380

Tyr Gln Val Ser Ala Gly Glu Val Leu Cys Gly Tyr Gln Pro Leu Ala
385                 390                 395                 400

Met Arg Asp Pro Glu Val Phe Glu Arg Pro Glu Phe Val Pro Glu
                405                 410                 415

Arg Phe Leu Gly Asp Glu Gly Ala Arg Leu Leu Gln His Leu Phe Trp
            420                 425                 430

Ser Asn Gly Pro Glu Thr Ala Gln Pro Gly Pro Gly Asn Lys Gln Cys
            435                 440                 445

Ala Ala Lys Glu Val Val Asp Thr Ala Cys Met Leu Leu Ala Glu
            450                 455                 460

Leu Phe Arg Arg Tyr Asp Asp Phe Glu Val Glu Gly Thr Ser Phe Thr
465                 470                 475                 480

Lys Leu Val Lys Arg Gln Ala Ser Pro Ser Val Ala Gln Ala Ala Ala
                485                 490                 495

Ala Ala Gly Ala Gln Gln
            500

<210> SEQ ID NO 2
<211> LENGTH: 1835
```

```
<212> TYPE: DNA
<213> ORGANISM: Zea mays
<220> FEATURE:
<221> NAME/KEY: 5'UTR
<222> LOCATION: (1)..(115)
<220> FEATURE:
<221> NAME/KEY: misc_feature
<222> LOCATION: (1025)..(1027)
<223> OTHER INFORMATION: I-helix
<220> FEATURE:
<221> NAME/KEY: misc_binding
<222> LOCATION: (1457)..(1459)
<223> OTHER INFORMATION: Heme-binding site
<220> FEATURE:
<221> NAME/KEY: 3'UTR
<222> LOCATION: (1625)..(1835)

<400> SEQUENCE: 2
```

| | | | | | |
|---|---|---|---|---|---|
| aattcggcac | gagctgagct | gagctgagct | gagctcacca | ccaccacaca | cgggagatag    60 |
| ctatagctag | catagcaagc | cagccagtca | gcgacttagc | agcagctagc | tagccatgct   120 |
| gccgtccttc | gtgtcgccga | cggcgagcgc | cgcggcctcg | gtgacgcctc | cgccgcggcc   180 |
| gataccagge | agctacgggc | caccggtgct | gggcccgcta | cgggaccggc | tcgactactt   240 |
| ctggttccag | agccaggacg | agttcttccg | gaagcgcgcg | gcggcacacc | gcagcaccgt   300 |
| gttccgcacc | aacatcccgc | ccaccttccc | cttcttcgtg | ggcgtggacc | cgcgcgtggt   360 |
| cgccatcgtg | gacgccgccg | ccttcaccgc | gctcttcgac | ccggacctcg | tggacaagcg   420 |
| cgacatcctc | atcgggccct | ataacccggg | cgccggcttc | accggcggga | cgcgcgtcgg   480 |
| cgtgtacctc | gacacgcagg | aggaggagca | cgcgcgcgtc | aagaccttcg | ccatggacct   540 |
| cctccaccgc | tccgcccgca | cctggtccgc | cgacttccgc | gcgagcgtcg | gcgccatgct   600 |
| ggacgccgtg | gacgcggagt | tcggcaagga | cgacggcagc | gacaagaagc | cctccgccag   660 |
| ctacctcgtc | ccgctgcagc | agtgcatctt | ccggttcctc | tgcaaggcgt | tcgtgggcgc   720 |
| cgacccgtcc | gccgactggc | tggtggacaa | cttcggcttc | accatcctgg | acatctggct   780 |
| ggcgctgcag | atcctgccca | cgcagaagat | cggcctcgtc | cagccgctgg | aggagctgct   840 |
| catccactcg | ttcccgctgc | cctccttcct | catctggccg | ggctactacg | tgctctaccg   900 |
| cttcatcgag | aagcacggcg | ccgaggccgt | ggcctacgcc | gaggcgcagc | acggcatcgg   960 |
| caagaaggac | gccatcaaca | acatcctgtt | cgtgctcggc | ttcaacgcct | tcggcggctt  1020 |
| ctccgtgttc | ctgcccttcc | tcgtggccaa | ggtcggcggc | gccccggcgc | tgcgcgagcg  1080 |
| gctgcgggac | gaggtgcggc | gcgccatggt | gggcaaagac | ggcgagttcg | ggttcgccac  1140 |
| cgtccgcgag | ggcatgccgc | tggtgcggtc | gacggtgtac | gagatgctgc | ggatgcagcc  1200 |
| gcccgtgccg | ctgcagttcg | ggcgcgcgcg | cagggacttc | gtgctgcgct | cccacggcgg  1260 |
| cgccgcgtac | caggtgtccg | cggcgaggt | gctgtgcggg | taccagccgc | tggcgatgcg  1320 |
| ggaccccgag | gtgttcgagc | ggcccgagga | gttcgtgccg | gaacgcttcc | tcggcgacga  1380 |
| gggcgccagg | ctgctgcagc | acctcttctg | gtccaacggg | ccggagacgg | cgcagcccgg  1440 |
| gcccgggaac | aagcagtgcg | ccgccaagga | ggtggtggtg | gacacggcgt | gcatgctgct  1500 |
| ggccgagctg | ttccggcgct | acgacgactt | cgaggtggag | ggcacctcct | tcaccaagct  1560 |
| cgtcaagcgc | caggcgtcgc | cgagcgtggc | gcaggcagca | gccgccgccg | gagcgcagca  1620 |
| gtgagtgcgc | tgtataggat | ccatcggtgg | cgtgcgacgt | cgccggcgcc | ggcgccggcc  1680 |
| aagcaataaa | gtaatgagta | ggccctcctc | gtcatccaca | tgctcgtctg | tgttcgactt  1740 |

-continued

```
cgatcggtgt ctcttcctcc cggccggccg ctggccgcca aacagccgtt gtggtaataa    1800
aaaaacactt gtggaaaaaa aaaaaaaaaa aaaac                               1835
```

HYDROPEROXIDE LYASE GENE FROM MAIZE AND METHODS OF USE

CROSS-REFERENCE TO RELATED APPLICATIONS

This application claims the benefit of U.S. Provisional Application No. 60/104,084, filed Oct. 13, 1998.

FIELD OF THE INVENTION

The invention relates to the genetic manipulation of plants, particularly to the expression of hydroperoxide lyase (HPL) genes in transformed plants.

BACKGROUND OF THE INVENTION

Plants produce volatile aldehydes via the oxylipin pathway; first converting a fatty acid to a hydroperoxy fatty acid by the action of a lipoxygenase, and subsequently cleaving the hydroperoxy fatty acid into a volatile aldehyde and an aldehyde acid by the action of a hydroperoxide lyase (HPL). For example, via the oxylipin pathway, linoleic acid converted to its hydroperoxy form is subsequently cleaved by HPL to yield the volatile 6 carbon aldehyde N-hexanal and 12-oxo-9Z-dodecenoic acid.

Similarly, linolenic acid converted to its hydroperoxy form is cleaved by HPL to yield 3Z-hexenal and 12-oxo-9Z-dodecenoic acid. 3Z-hexenal is further converted to 2E-Hexenal (leaf aldehyde) by an isomerase factor. HPL also catalyzes formation of 9-carbon aldehydes such as nonadienal and the corresponding nonanoic acid. Action of an alcohol dehydrogenase converts the oxylipin pathway-derived aldehydes to their corresponding alcohols; for example hexanol, hexenol or nonadienol. A review of volatile aldehyde formation in plants is provided in Hatanaka et al (1986) *Biogeneration of Aromas*, American Chemical Society, 167–175, the contents of which are herein incorporated by reference.

Food toxicoses affect human and animal health worldwide. Aflatoxin contamination has been identified as a result of fungal infection with the *Aspergillus flavus* (*A. flavus*) group in many foods, including corn grown in Southeastern United States. Lack of aflatoxin contamination in early stages of corn development is associated with presence of volatile metabolites at peak concentrations. Naturally occurring volatile aldehydes inhibit *A. flavus* growth in corn (Gueldner et al. (1985) *J. Agric. Food Chem.* 33(3) :411–413); and the exceptional natural resistance of soybeans to *A. flavus* may be attributed to generation of volatile aldehydes, particularly hexanal (Doehlert et al. (1993) Abstract, American Phytophathological Society 83(12): 1473–1477). A relationship between aflatoxin resistance, and volatile aldehyde, and precursor fatty acid content, has been reported in studies of aflatoxin-susceptible and -resistant maize (Zeringue, Jr. et al. (1996) *J. Agric. Food Chem.* 44:403–407). However, a concentration-dependent toxicity to higher plants has also been shown to be associated with volatile aldehydes (Gardner et al. (1990) *J. Agric. Food Chem.* 38:1316–1320).

Volatile aldehydes can inhibit growth of fungal cultures of *Colletotrichum truncatum*, *Rhizoctonia solani* and *Sclerotium rolfsii* (Vaughn et al. (1993) *Journal of Chemical Ecology* 19(10):2337–2345). Furthermore, volatile aldehydes can exhibit antibacterial activity and are implicated in protection against mechanical wounding; for example, insect-induced wounding (Matsui et al. (1996) FEBS Letters 394:21–24; Shibata et al (1995) *Plant Cell Physiol.* 36(1): 147–156; Blée et al. (1996) *Plant Physiol.* 110:445–154).

Six carbon aldehydes, together with their corresponding alcohols are responsible for the characteristic odor of green leaves, and are also constituents of aroma and flavor from various fruits. As such aroma and flavor compounds, the aldehydes are also referred to as natural "green note" compounds (Hatanaka et al. (1986) *Biogeneration of Aromas*, American Chemical Society, 167–175; Götz-Schmidt et al. (1986) *Lebensm.-Wiss. u.-Technol.* 19(2):152–155; EP 0 801 133 A2; Matsui et al. (1996) *FEBS Letters* 394:21–24).

HPL is distributed in a variety of plant species in membrane bound forms; both chloroplastic and non-chloroplastic. HPL has been purified from both non-green and green tissue; including fruits of pear, tomato, cucumber, cultured cells of tobacco, and tea leaves (Hatanaka et al. (1986) *Biogeneration of Aromas*, American Chemical Society, 167–175; Götz-Schmidt et al. (1986) *Lebensm.-Wiss. u.-Technol* 19(2):152–155). It has been suggested that two forms of HPL exist; one is common to both green and non-green cells and another is chloroplast-specific (Sekiya et al. (1984) *Phytochemistry* 23(11):2439–2443). HPL-like activity has also been observed in non-plant microbial sources (Bisakowski et al. (1997) *Biosci. Biotech. Biochem.* 61(8):1262–1269).

While the biochemistry and tissue distribution of HPL is well characterized, data regarding molecular biology of HPL is sparse. HPL has been cloned from bell pepper. Sequence analysis of the clone shows C-terminal homology to members of the cytochrome P450 family, particularly to allene oxide synthase. Heme- and oxygen-binding domains have been identified in this sequence (Matsui et al. (1996) *FEBS Letters* 394:21–244). HPL has also been cloned from banana leaf as described in EP 0 801 133 A2, and from Arabidopsis as described in Bate et al. (1998) *Plant Physiol* 117(4) :1393–1400; although no DNA sequence is described for the Arabidopsis HPL clone.

Due to the role of volatile aldehydes in disease resistance, pathogen protection, and modulation of aroma and flavor, it would be beneficial to influence levels of volatile aldehyde and related compounds by manipulating HPL levels in a plant.

SUMMARY OF THE INVENTION

Compositions and methods for expressing hydroperoxide lyase (HPL) genes in plants, plant cells, and plant tissues are provided. The compositions comprise nucleotide sequences encoding maize HPL genes. The sequences are useful in transforming plants for tissue-preferred or constitutive expression of HPL. Such sequences find use in enhancing disease resistance and in modulating levels of flavor molecules in plants.

Expression cassettes comprising the HPL sequences of the invention are provided. Additionally provided are transformed plant cells, plant tissues, and plants.

BRIEF DESCRIPTION OF THE DRAWINGS

FIG. 3 depicts a vector construct for expression of HPL comprising a ubiquitin promoter, HPL gene of the invention, PINII terminator, and PAT selectable marker.

DETAILED DESCRIPTION OF THE INVENTION

Figure 1:
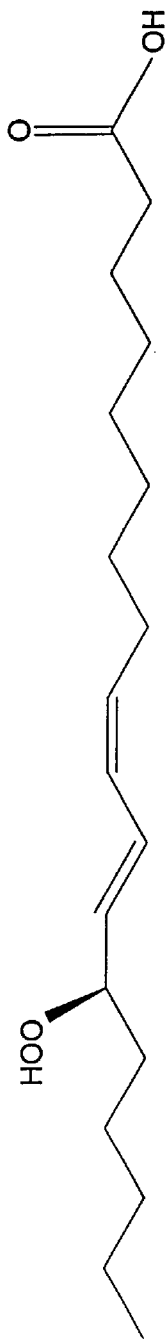
FIG. 1 depicts HPL catalyzed production of volatile hexanal from 13-hydroperoxy-linoleic acid.
Figure 1:
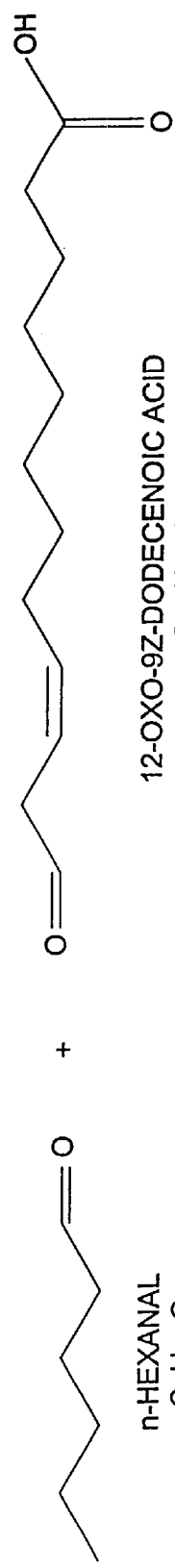

The present invention is drawn to compositions and methods for expressing hydroperoxide lyase (HPL) genes in plants, plant cells, and specific plant tissues. The compositions include nucleic acids and proteins relating to HPL genes in plants.

More particularly, compositions of the invention include the native nucleotide sequence for a cereal HPL gene. Examples of cereals include but are not limited to maize, rice, wheat, barley, sorghum, rye and the like. Even more particularly, a maize HPL gene and the respective amino acid sequence for the HPL protein encoded thereby, as well as fragments and variants thereof are provided. The maize sequences are set forth in SEQ ID NO:1 and 2.

These sequences or the corresponding antisense sequences find use in modulating the expression of HPL in a plant or plant cell. That is, the coding sequences are used to increase the expression while antisense sequences are used to decrease expression. The sequences find use in the construction of expression vectors for subsequent transformation into plants of interest, in methods for enhancing disease resistance in plants, in methods for modulating levels of flavor molecules in plants, as probes for the isolation of other HPL-like genes, as molecular markers, and the like.

Compositions of the invention include nucleotide sequences encoding enzymes that are involved in cleavage of hydroperoxy-fatty acids. In particular, the present invention provides for isolated nucleic acid molecules comprising nucleotide sequences encoding the amino acid sequences shown in SEQ ID NO: 1, or the nucleotide sequences encoding the DNA sequences deposited in a bacterial host as Patent Deposit Nos. 98746. Further provided are polypeptides having an amino acid sequence encoded by a nucleic acid molecule described herein, for example those set forth in SEQ ID NO: 2, those deposited in a bacterial host as Patent Deposit No. 98746, and fragments and variants thereof.

Plasmids containing the nucleotide sequences of the invention were deposited with the Patent Depository of the American Type Culture Collection (ATCC), Manassas, Va., and assigned Patent Deposit No. 98746. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence cleave a hydroperoxy-fatty acid to yield an aldehyde and an aldehyde acid. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a nucleotide sequence that encodes a biologically active portion of a protein of the invention will encode at least 15, 25, 30, 50, 100, 150, 200, or 250 contiguous amino acids, or up to the total number of amino acids present in a full-length HPL protein of the invention (for example, 502 amino acids for SEQ ID NO: 1. Fragments of a HPL nucleotide sequence that are useful as hybridization probes or PCR primers generally need not encode a biologically active portion of a HPL protein.

Thus, a fragment of a nucleotide sequence may encode a biologically active portion of a HPL protein, or it may be a fragment that can be used as a hybridization probe or PCR primer using methods disclosed below. A biologically active portion of a HPL protein can be prepared by isolating a portion of one of the nucleotide sequences of the invention, expressing the encoded portion of the HPL protein (e.g., by recombinant expression in vitro), and assessing the activity of the encoded portion of the HPL protein. Nucleic acid molecules that are fragments of a nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400 nucleotides, or up to the number of nucleotides present in a full-length HPL nucleotide sequence disclosed herein (for example, 1835 nucleotides for SEQ ID NO: 2.

By "variants" is intended substantially similar sequences. For nucleotide sequences, conservative variants include those sequences that, because of the degeneracy of the genetic code, encode the amino acid sequence of one of the HPL polypeptides of the invention. Naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a HPL protein of the invention. Generally, variants of a particular nucleotide sequence of the invention will have at least 40%, 50%, 60%, 70%, generally at least 75%, 80%, 85%, preferably about 90% to 95% or more, and more preferably about 98% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, the hyhydroproxide-fatty acid cleaving activity as described herein. Such variants may result from, for example, genetic polymorphism or from human manipulation. Biologically active variants of a native protein of the invention will have at least 40%, 50%, 60%, 70%, generally at least 75%, 80%, 85%, preferably about 90% to 95% or more, and more preferably about 98% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the HPL proteins can be prepared by mutations in the DNA. Methods for mutagenesis and nucleotide sequence alterations are well known in the art. See, for example, Kunkel (1985) *Proc. Natl. Acad Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof Such variants will continue to possess the desired hydroperoxide-fatty acid cleaving activity. Obviously, the mutations that will be made in the DNA encoding the variant must not place the sequence out of reading frame and preferably will not create complementary regions that could produce secondary MRNA structure. See, EP Patent Application Publication No. 75,444.

The deletions, insertions, and substitutions of the protein sequence encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assessing hydroperoxide lyase activity as described herein.

Variant nucleotide sequences and proteins also encompass sequences and proteins derived from a mutagenic and recombinogenic procedure such as DNA shuffling. With such a procedure, one or more different HPL coding sequences can be manipulated to create a new HPL possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the HPL gene of the invention and other known HPL genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

Figure 2:
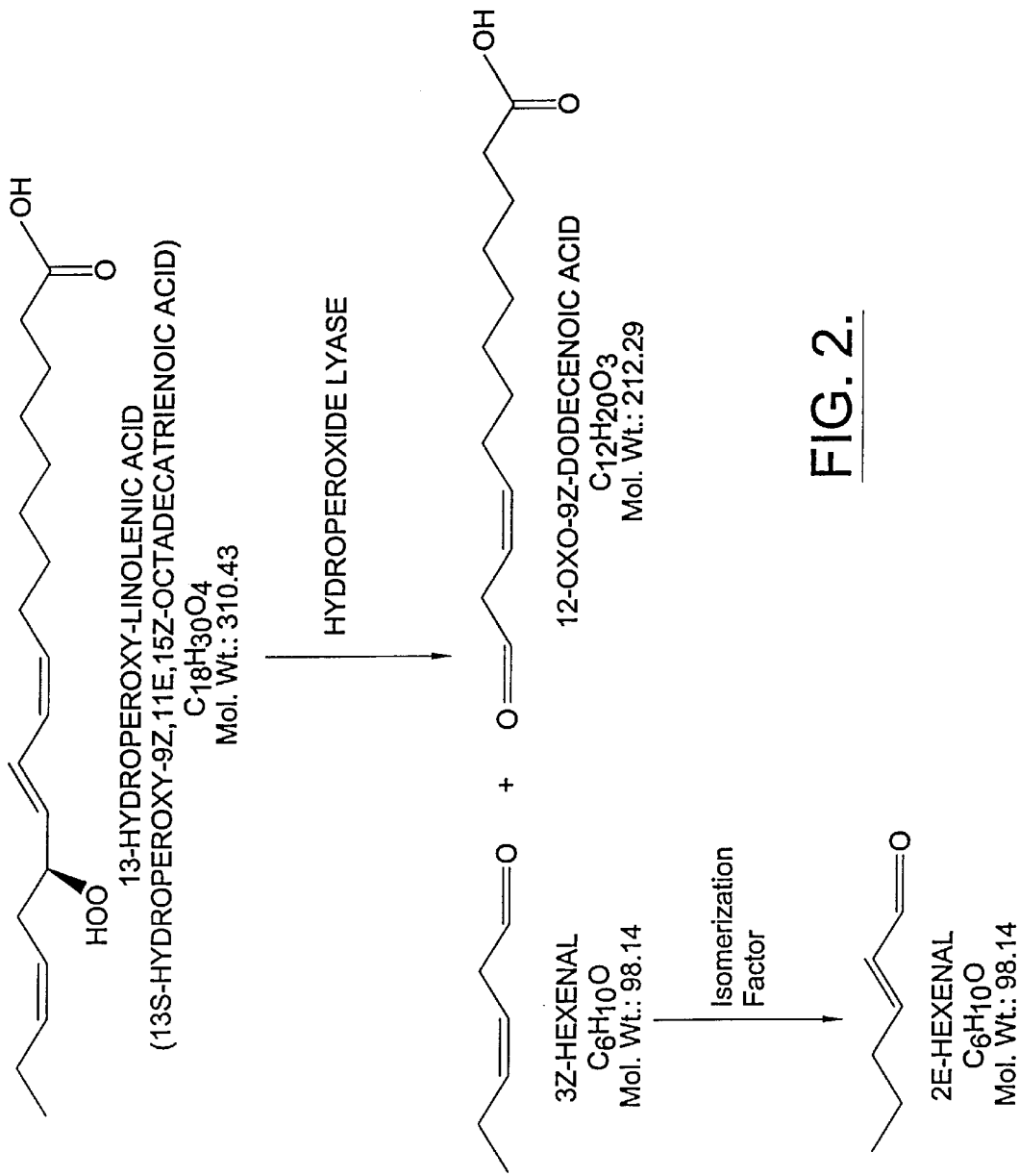
FIG. 2 depicts HPL catalyzed production of volatile hexenal from 13-hydroperoxy-linolenic acid.

The invention encompasses biologically active fragments and variants of the protein sequences disclosed herein. Such biologically active fragments and variants will have hydroperoxide lyase activity. That is, such fragments and variants will cleave a hydroperoxy-fatty acid to yield an aldehyde and an aldehyde acid. Such hydroperoxy-fatty acids include but are not limited to 18-carbon hydroperoxy-fatty acids including but not limited to 9-, 12- and 13-hydroperoxyfatty acids. Such aldehydes include but are not limited to hexanal, hexenal and nonadienal. Particular examples of hydroperoxy-fatty acid HPL cleavage substrates, and the aldehyde and aldehyde acid cleavage products are provided in FIGS. 1 and 2, and in the following references, the contents of which are herein incorporated by reference: EP 0 801 133 A2; Bisakowski et al. (1997) *Biosci. Biotech. Biochem.* 6(8):1262–1269; Sekiya et al. (1984) *Phytochemistry* 23(11):2439–2443; Matsui et al. (1996) *FEBS Letters* 394:21–24; Shibata et al. (1995) *Plant Cell Physiol.* 36 (1):147–156; Götz-Schmidt et al. (1986) *Lebensm.-Wiss. u.-Technol.* 19(2):152–155; Blée et al. (1996) *Plant Physiol.* 110:445–154; Vick (1991) *LIPIDS* 26(4):315–320; Sekiya et al. (1983) *Phytochemistry* 22(9):1867–1869; Vaughn et al. (1993) *Journal of Chemical Ecology* 19(10):2337–2345; Zeringue, Jr. et al. (1996) *J. Agric. Food Chem.* 44:403–407; Hatanaka et al. (1986) *Biogeneration of Aromas*, American Chemical Society, 167–175; Gueldner et al. (1985) *J. Agric. Food Chem.* 33(3):411–413; Gardner (1970) *Journal of Lipid Research* 11:311–321; Gardner et al. (1990) *J. Agric. Food Chem.* 38:1316–1320. Methods for determination of HPL activity, as well as for isolation, characterization, and quantitation of direct and downstream products of HPL catalysis are readily available to those ordinarily skilled in the art, for example, as described in the above-listed references.

It is recognized that the invention encompasses influencing production of downstream metabolites of HPL catalysis, which are produced not as a direct product of an HPL catalyzed reaction, but as a result of a subsequent reaction of a series of reactions, involving a product of HPL catalysis. These reactions include spontaneous, factor-induced or enzyme-catalyzed isomerization. Thus, the production of these downstream metabolites could be influenced by modulating the expression of HPL.

More specifically, it is recognized that the invention encompasses production of aldehydes which are not a direct product of the cleavage action of HPL proteins, but are produced by isomerization of such aldehydes. For example, isomerization of 3Z-hexenal to 2E-hexenal as provided in FIG. 2.

It is also recognized that the invention encompasses production of alcohols corresponding to the aldehydes produced by HPL proteins of the invention, and/or corresponding to aldehydes produced as a result of isomerization of such aldehydes. Such alcohols are typically produced by the action of an alcohol dehydrogenase. For example, see FIG. 1 of Hatanaka et al. (1986) *Biogeneration of Aromas*, American Chemical Society, 167–175, in which (3-Z)-hexanal and (2E)-Hexenal are respectively converted to (3Z)-hexanol and (2E)-hexenol.

The sequences of the invention are useful to transform plants and manipulate the concentration of volatile compounds in plants. By "volatile compound" is intended the aldehydes and/or alcohols that are produced as described above and which are capable of being readily vaporized.

The sequences of the invention are also useful to transform plants and modulate levels of flavor molecules in plants. By "flavor molecules" is intended aldehydes and/or alcohols that are produced and are constituents of odor and/or taste in plants. In particular, flavor molecules include certain volatile alcohols and aldehydes. Examples of such flavor molecules which are also volatile include but are not limited to hexanal, (3Z)-hexenal, (2E)-hexenal, (3Z)-hexenol, (3Z, 6Z)-nonadienal, (2E, 6Z)-nonadienal. By "modulating levels of flavor molecules" is intended an increase or a decrease in the amount of such molecules.

Thus, influencing the production of direct or downstream products of HPL catalysis by modulating expression of HPL is encompassed by the invention; and specific examples of such products include but are not limited to hexanol, hexanal, dodecenoic acid, nonanoic acid, nonadienal, nonadienol, hexenol, hexenal, cis-3-hexenol, cis-3-hexenal, 12-oxo-cis-9-dodecenoic acid, cis-3-cis-6-nonadienal, 9-oxononanoic acid, trans-2-hexenol, trans-2-hexenal, 12-oxo-trans-10-dodecenoic acid (traumatin), trans-2-cis-6-nonadienal, trans-2-cis-6-nonadienol, trans-2-dodecedioic acid (traumatic acid), 1-octen-3-ol, 10-oxo-8-decenoic acid, 13-oxo-tridecadienoic acid, pentane or pentene, nonenal, pentanol, 13-oxodienoic acid, 3-octanol, 2-octen-1-ol, 1-octanol, (E)-2-nonenal, and (Z)-3-nonenal and (E)-4-Hydroxy-2-nonenal (HNE).

The nucleotide sequences encoding the HPL proteins of interest can be the naturally occurring sequence cloned from maize, or they may be synthetically derived sequences.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire HPL sequences set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the HPL sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire HPL sequence disclosed herein, or one or more portions thereof, may be used as a probe capable of specifically hybridizing to corresponding HPL sequences and messenger RNAs. To achieve specific hybridization under a variety of conditions, such probes include sequences that are unique among HPL sequences and are preferably at least about 10 nucleotides in length, and most preferably at least about 20 nucleotides in length. Such probes may be used to amplify corresponding HPL sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the Tm can be approximated from the equation of Meinkoth and Wahl (1984) *Anal. Biochem.* 138:267–284: $T_m$=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for a HPL protein and which hybridize under stringent conditions to the HPL sequences disclosed herein, or to fragments thereof, are encompassed by the present invention. Such sequences will be at least 40% to 50% homologous, about 60% to 70% homologous, and even about 75%, 80%, 85%, 90%, 95% to 98% homologous or more with the disclosed sequences. That is, the sequence identity of sequences may range, sharing at least 40% to 50%, about 60% to 70%, and even about 75%, 80%, 85%, 90%, 95% to 98% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mot Biol.* 48:443–453; the search-for-similarity-method of Pearson and Lipman (1988) *Proc. Natl. Acad Sci.* 85:2444–2448; the algorithm of Karlin and Altschul (1990) *Proc. Natl. Acad Sci. USA* 872264, modified as in Karlin and Altschul (1993) *Proc. Natl. Acad Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection. Alignment may also be performed manually by inspection.

For purposes of the present invention, comparison of nucleotide or protein sequences for determination of percent sequence identity to the HPL sequences disclosed herein is preferably made using BLASTN or BLASTX programs respectively (BLAST Version 2.0 or later) with their respective default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The sequences of the invention are useful to transform plants and enhance disease resistance in plants. The invention is drawn to compositions and methods for inducing resistance in a plant to plant pests. Accordingly, the compositions and methods are also useful in protecting plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened. The methods of the invention can be utilized to protect plants from disease, particularly those diseases that are caused by plant pathogens.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia scierotiorum, Fusarium oxysporum, Diaporthe phaseolorum* var. *sojae* (*Phomopsis sojae*), *Diaporthe phaseolorum* var. *caulivora, Scierotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium*

*aphanidermatum, Pythium ultimum, Pythium debaryanum,* Tomato spotted wilt virus, *Heterodera glycines Fusarium solani;* Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;* Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis,* Fusarium, *Xanthomonas campestris* p.v. *alfalfae, Aphanomyces euteiches, Stemphylium herbarum, Stemphylium alfalfae;* Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora triticirepentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Clavice pspurpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophominaphaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis;* Corn: *Fusarium moniliforme* var. *subglutinans, Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillus flavus, Bipolaris maydis O, T (Cochliobolus heterostrophus), Helminthosporium carbonum I, II & III (Cochliobolus carbonum), Exserohilum turcicum I, II & III, Helminthosporium pedicellatum, Physoderma maydis, Phyllosticta maydis, Kabatiella maydis, Cercospora sorghi, Ustilago maydis, Puccinia sorghi, Puccinia polysora, Macrophominaphaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora,* Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola (Glomerella graminicola), Cercospora sorghi, Gloeocercospora sorghi, Ascochyta sorghina, Pseudomonas syringae* p.v. *syringae, Xanthomonas campestris* p.v. *holcicola, Pseudomonas anaropogonis, Pucciniapurpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronoscierospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root-knot, cyst, and lesion nematodes, including Heterodera and Globodera spp; particularly *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis,* European corn borer; *Agrotis ipsilon,* black cutworm; *Helicoverpa zea,* corn earworm; *Spodoptera frugiperda,* fall armyworm; *Diatraea grandiosella,* southwestern corn borer; *Elasmopalpus lignosellus,* lesser cornstalk borer; *Diatraea saccharalis,* surgarcane borer; *Diabrotica virgifera,* western corn rootworm; *Diabrotica longicornis barberi,* northern corn rootworm; *Diabrotica undecimpunctata howardi,* southern corn rootworm; Melanotus spp., wireworms; *Cyclocephala borealis,* northern masked chafer (white grub); *Cyclocephala immaculata,* southern masked chafer (white grub); *Popillia japonica,* Japanese beetle; *Chaetocnema pulicaria,* corn flea beetle; *Sphenophorus maidis,* maize billbug; *Rhopalosiphum maidis,* corn leaf aphid; *Anuraphis maidiradicis,* corn root aphid; *Blissus leucopterus leucopterus,* chinch bug; *Melanoplus femurrubrum,* redlegged grasshopper; *Melanoplus sanguinipes,* migratory grasshopper; *Hylemya platura,* seedcorn maggot; *Agromyza parvicornis,* corn blot leafminer; *Anaphothrips obscrurus,* grass thrips; *Solenopsis milesta,* thief ant; *Tetranychus urticae,* twospotted spider mite; Sorghum: *Chilo partellus,* sorghum borer; *Spodoptera frugiperda,* fall armyworm; *Helicoverpa zea,* corn earworm; *Elasmopalpus lignosellus,* lesser cornstalk borer; *Feltia subterranea,* granulate cutworm; *Phyllophaga crinita,* white grub; Eleodes, Conoderus, and Aeolus spp., wireworms; *Oulema melanopus,* cereal leaf beetle; *Chaetocnema pulicaria,* corn flea beetle; *Sphenophorus maidis,* maize billbug; *Rhopalosiphum maidis;* corn leaf aphid; *Sipha flava,* yellow sugarcane aphid; *Blissus leucopterus leucopterus,* chinch bug; *Contarinia sorghicola,* sorghum midge; *Tetranychus cinnabarinus,* carmine spider mite; *Tetranychus urticae,* twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hyperapunctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; Delia ssp., Root maggots.

Naturally occurring volatile aldehydes inhibit growth of certain pathogens on plants, and natural resistance of some plants to a particular pathogen can be attributed to generation of voltile aldehydes. Thus, the sequences of the invention are useful to transform plants to express HPL and produce volatiles thereby to treat pathogen-mediated contamination of plants, particularly food and feed crops. By "treating pathogen-mediated contamination" is intended prevention, reduction, amelioration or elimination in a plant, plant tissue or cell, of the presence of a pathogen, a product of a pathogen, or a product of the plant-pathogen interaction. More particularly, the invention encompasses treating pathogen-mediated contamination of stored food and feed crops, including but not limited to stored grain. Even more particularly, the invention encompasses Aspergillus flavus-mediated aflatoxin contamination of stored corn.

For transforming plants, the HPL sequences of the invention may be utilized in expression cassettes with constitutive or tissue-preferred promoters. Constitutive promoters would provide a constant production of HPL and thereby products of HPL catalysis including volatiles, and downstream products throughout the plant. Such constitutive promoters include, for example, the core promoter of the Rsyn7 (copending U.S. patent application Ser. No. 08/661,601), the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619– 632 and Christensen et al. (1992) *Plant Mol Biol* 18:675–689); pEMU (Last et al. (1991) *Theor. Appl. Genet.* 81:581–588); MAS (Velten et al. (1984) *EMBO J.* 3:2723–2730); ALS promoter (U.S. patent application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142.

The utilization of tissue-preferred promoters would increase or decrease the expression of HPL in specific tissues of the plant. It is recognized that in modulating the levels of flavor molecules, it may be desirable to increase or decrease the levels of such molecules in a particular tissue. It is also recognized that in enhancing disease resistance, tolerance of various tissues to increased expression of HPL may vary; thus, it may be desirable to increase expression in selected tissues, or at varying levels in different tissues by the use of tissue-preferred promoters. For example, leaf-specific promoters may be utilized. Such tissue-preferred promoters include those described in: Yamamoto et al. (1997) *Plant J.* 12(2):255–265; Kawamata et al. (1997) *Plant Cell Physiol.* 38(7):792–803; Hansen et al. (1997) *Mol. Gen. Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol. Biol.* 23(6):1129–1138; Matsuoka et al. (1993) *Proc. Natl. Acad Sci. USA* 90(20):9586–9590; and Guevara-Garcia et al. (1993) *Plant J.* 4(3):495–505.

Another tissue-preferred promoter of interest includes root-preferred promoters. The utilization of such promoters would provide a method of selectively enhancing disease resistance and/or modulating levels of flavor molecules in the root. Such enhancement and/or modulation may be particularly desirable in plants in which the root constitutes the food crop, including, but not limited to carrot, potato, radish, and the like. Such root-preferred promoters include the VfENOD-GRP3 gene promoter (Kuster H et al. (1995) *Plant Mol. Biol.* 29(4):759–772); and rolB promoter (Capana et al. (1994) *Plant Mol. Biol* 25 (4):681–691. See also U.S. Pat. Nos. 5,633,363; 5,459,252; 5,401,836; 5,110, 732; and 5,023,179.

Seed-preferred promoters includes both seed-specific promoters (those promoters active during seed development) as well as seed-germinating promoters (those promoters active during seed germination). Such promoters include Cim1 (cytokinin-induced message); cZ19B1 (maize 19KDa zein); milps (myo-inositol-1-phosphate synthase); celA (cellulose synthase); end1 (*Hordeum verlgase* mRNA clone END1); and imp3 (myo-inositol monophosphate-3). For dicots, particular promoters include phaseolin, napin, β-conglycinin, soybean lectin, and the like. For monocots, particular promoters include maize 15Kd zein, 22KD zein, 27kD zein, waxy, shrunken 1, shrunken 2, globulin 1, etc.

In green plants, HPL protein and activity is associated with chloroplasts. For example, see Sekiya et al. (1984) *Phytochemistry* 23(11):2439–2443; Götz-Schmidt et al. (1986) *Lebensm.-Wiss. u.-Technol.* 19(2):152–155. Thus, it may be beneficial to influence the expression of HPL proteins of the invention in chloroplasts. Such may be accomplished either by including a chloroplast targeting signal, which functions to direct the protein into the chloroplast, or to directly transform the chloroplast to express the gene of interest. Chloroplast targeting sequences are known in the art and include the chloroplast small subunit of ribulose-1, 5-bisphosphate carboxylase (Rubisco), (de Castro Silva Filho et al. (1996) *Plant Mol. Biol.* 30:769–780; Schnell, et al. (1991) *J. Biol. Chem.* 266(5):3335–3342); 5-(enolpyruvyl)shikimate-3-phosphate synthase (EPSPS) (Archer et al. (1990) *J. Bioenerg. Biomemb.* 22(6) :789–810); tryptophan synthase (Zhao et al. (1995) *J. Biol. Chem.* 270(11):6081–6087); plastocyanin (Lawrence et al. (1997) *J. Biol. Chem.* 272(33):20357–20363); chorismate synthase (Schmidt et al. (1993) *J. Biol. Chem.* 268(36) :27477–27457); and the light harvesting chlorophyll a/b binding protein (LHBP) (Lamppa et al. (1988) *J. Biol. Chem.* 263:14996–14999). See also Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and Shah et al. (1986) *Science* 233:478–481.

Likewise, methods for transformation of chloroplasts are known in the art. See, for example, Svab et al. (1990) *Proc. Natl. Acad. Sci. USA* 87:8526–8530; Svab and Maliga (1993) *Proc. Natl Acad. Sci. USA* 90:913–917; Staub and Maliga (1993) *Embo J.* 12:601–606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301–7305.

Sequences of the invention as provided by SEQ ID NOS:1 and 2 comprise heme- and oxygen-binding domains and show the greatest homology to bell pepper HPL as described in Matsui et al. (1996) *FEBS Letters* 394:21–24, the contents of which are herein incorporated by reference. Thus, it is recognized that expression of the sequences of the invention could influence oxygen metabolism and transport in a plant and further influence productivity of particular pathways in the plant. Such pathways are influenced because of the change in availability of oxygen. Such changes in amounts of oxygen may generally work to affect the flux of biosynthetic routes in plants. Therefore, expression of the sequences of the invention may influence the production of a secondary metabolite of interest in a plant or plant cell culture. Such secondary metabolites include such classes of compounds as the indoles, phenolics, phenylpropanoids, flavanoids, alkaloids, isoprenoids, glucosinolates, and the like. More specific examples include cis-1, 4-polyisoprene, polyacetylenes, thiophenes, taxanes (taxol), 3-thiazol-2'yl-indole (camalexin), acetylsalicylate, and the like.

The HPL sequences of the invention can be introduced into any plant. The sequences to be introduced may be used in expression cassettes for expression in any plant of interest. The HPL sequences of the invention are provided in expression cassettes for expression in the plant of interest. The cassette will include 5' and 3' regulatory sequences operably linked to a HPL sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the HPL sequence to be under the transcriptional regulation of the regulatory regions. The expression cassette may additionally contain selectable marker genes.

Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention The expression cassette will include in the 5'-3' direction of transcription, a transcriptional and translational initiation region, a HPL DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of HPL in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogenetal. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picomavirus leaders, for example, EMCV leader (Encephalomyocarditis 5' noncoding region) (Elroy-Stein et al. (1989) *Proc. Natl. Acad. Sci. USA* 86:6126–6130); potyvirus leaders, for example, TEV leader (Tobacco Etch Virus) (Gallie et al. (1995) *Gene* 165(2):233–238), MDMV leader (Maize Dwarf Mosaic Virus) (*Virology* 154:9–20), and human immunoglobulin heavy-chain binding protein (BiP) (Macejak et al. (1991) *Nature* 353:90–94); untranslated leader from the coat protein MRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

It is recognized that with the nucleotide sequences of the present invention, antisense constructions complementary to at least a portion of the messenger RNA (mRNA) for the HPL sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The sequences of the present invention can be used to transform or transfect any plant. In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and*

*Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P: 175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The present invention may be used for transformation of any plant species, including, but not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indca*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Tuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The following examples are offered by way of illustration and not by way of limitation.

EXPERIMENTAL

EXAMPLE 1

Plasmid Constructs

Gene sequences are cloned into a plasmid vector, such as that shown in FIG. 3, in the sense orientation so that they are under the transcriptional control of the ubiquitin promoter. A selectable marker gene may reside on this plasmid or may be introduced as part of a second plasmid. The transformation construct is then available for introduction into maize embryos by bombardment methods as described in Example 2.

EXAMPLE 2

Transformation and Regeneration of Transgenic Plants

Immature maize embryos from greenhouse donor plants are bombarded with a plasmid containing the HPL gene of the invention operably linked to a ubiqitin promoter plus a plasmid containing the selectable marker gene PAT (Wohlleben et al. (1988) *Gene* 70:25–37) that confers resistance to the herbicide Bialaphos. Transformation is performed as follows. All media recipes are in the Appendix.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the operably linked to a HPL gene of the invention is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water

10 μl (1 μg) DNA in TrisEDTA buffer (1 μg total)

100 μl 2.5 M $CaCl_2$

10 μl 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total often aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored for expression of the HPL gene of interest. HPL activity is measured by methods known in the art, for example, as described in Vick (1991) *Lipids* 26: 315–320.

APPENDIX

272 V

| Ingredient | Amount | Unit |
| --- | --- | --- |
| D-I $H_2O$ | 950.000 | Ml |
| MS Salts (GIBCO 11117-074) | 4.300 | G |
| Myo-Inositol | 0.100 | G |
| MS Vitamins Stock Solution ## | 5.000 | Ml |
| Sucrose | 40.000 | G |
| Bacto-Agar @ | 6.000 | G |

Directions

@=Add after bringing up to volume

Dissolve ingredients in polished D-I $H_2O$ in sequence

Adjust to pH 5.6

Bring up to volume with polished D-I $H_2O$ after adjusting pH

Sterilize and cool to 60° C.

=Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.

Total Volume (L)=1.00

288 J

| Ingredient | Amount | Unit |
| --- | --- | --- |
| D-I $H_2O$ | 950.000 | Ml |
| MS Salts | 4.300 | G |
| Myo-Inositol | 0.100 | G |
| MS Vitamins Stock Solution ## | 5.000 | Ml |
| Zeatin .5 mg/ml | 1.000 | Ml |
| Sucrose | 60.000 | G |
| Gelrite @ | 3.000 | G |
| Indoleacetic Acid 0.5 mg/ml # | 2.000 | Ml |
| 0.1 mM Abscisic Acid | 1.000 | Ml |
| Bialaphos 1 mg/ml # | 3.000 | Ml |

Directions

@=Add after bringing up to volume

Dissolve ingredients in polished D-I $H_2O$ in sequence

Adjust to pH 5.6

Bring up to volume with polished D-I $H_2O$ after adjusting pH

Sterilize and cool to 60° C.

Add 3.5g/L of Gelrite for cell biology.

=Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence.

Bring up to volume with polished D-I H₂O. Make in 400 ml portions. Thiamine.HCL & Pyridoxine.HCL are in Dark Desiccator. Store for one month, unless contamination or precipitation occurs, then make fresh stock.
Total Volume (L) =1.00

560 R

| Ingredient | Amount | Unit |
|---|---|---|
| D-I Water, Filtered | 950.000 | Ml |
| CHU (N6) Basal Salts (SIGMA C-1416) | 4.000 | G |
| Eriksson's Vitamin Mix (1000X SIGMA-1511 | 1.000 | Ml |
| Thiamine HCL 0.4 mg/ml | 1.250 | Ml |
| Sucrose | 30.000 | G |
| 2, 4-D 0.5 mg/ml | 4.000 | Ml |
| Gelrite @ | 3.000 | G |
| Silver Nitrate 2 mg/ml # | 0.425 | Ml |
| Bialaphos 1 mg/ml # | 3.000 | Ml |

Directions
@=Add after bringing up to volume
=Add after sterilizing and cooling to temp.
Dissolve ingredients in D-I H₂O in sequence
Adjust to pH 5.8 with KOH
Bring up to volume with D-I H₂O
Sterilize and cool to room temp.
Total Volume (L)=1.00

560 Y

| Ingredient | Amount | Unit |
|---|---|---|
| D-I Water, Filtered | 950.000 | Ml |
| CHU (N6) Basal Salts (SIGMA C-1416) | 4.000 | G |
| Eriksson's Vitamin Mix (1000X SIGMA-1511) | 1.000 | Ml |
| Thiamine.HCL 0.4 mg/ml | 1.250 | Ml |
| Sucrose | 120.000 | G |
| 2,4-D 0.5 mg/ml | 2.000 | Ml |
| L-Proline | 2.880 | G |
| Gelrite @ | 2.000 | G |
| Silver Nitrate 2 mg/ml # | 4.250 | Ml |

Directions
@=Add after bringing up to volume
=Add after sterilizing and cooling to temp.
Dissolve ingredients in D-I H₂O in sequence
Adjust to pH 5.8 with KOH
Bring up to volume with D-I H₂O
Sterilize and cool to room temp.
 Autoclave less time because of increased sucrose
Total Volume (L)=1.00

That which is claimed:

1. An isolated nucleotide sequence selected from the group consisting of:
   (a) a nucleotide sequence encoding the amino acid sequence of SEQ ID NO:1; and
   (b) a nucleotide sequence set forth in SEQ ID NO:2.

2. An expression cassette comprising the nucleotide sequence of claim 1, wherein said nucleotide sequence is operably linked to a promoter that drives expression in a plant cell.

3. The expression cassette of claim 2, wherein said promoter is a tissue-preferred promoter.

4. The expression cassette of claim 3, wherein said promoter drives expression in tissue selected from the group consisting of root, seed, embryo, and green tissue.

5. The expression cassette of claim 2, wherein said promoter is a constitutive promoter.

6. The expression cassette of claim 5, wherein said constitutive promoter is a ubiquitin promoter.

7. The expression cassette of claim 2, wherein said promoter is a heterologous promoter.

8. The expression cassette of claim 2, wherein said cassette further comprises a chloroplast targeting sequence operably linked to said nucleotide sequence.

9. The expression cassette of claim 8, wherein said promoter is a constitutive promoter.

10. A method for modulating expression of hydroperoxide lyase in a transformed plant relative to an untransformed plant, said method comprising transforming a plant cell with at least one nucleotide sequence encoding a maize hydroperoxide lyase protein, and regenerating a stably transformed plant from said transformed plant cell, wherein said stably transformed plant has modulated hydroperoxide lyase expression relative to said untransformed plant, and wherein said nucleotide sequence is operably linked to a promoter that drives expression in said transformed plant, wherein said nucleotide sequence is selected from the group consisting of:
    (a) a nucleotide sequence encoding the amino acid sequence of SEQ ID NO:1; and
    (b) a nucleotide sequence set forth in SEQ ID NO:2.

11. A transformed plant cell having stably incorporated into its genome at least one nucleotide sequence encoding a hydroperoxide lyase protein, said nucleotide sequence operably linked to a heterologous promoter that drives expression in a plant cell, wherein said nucleotide sequence is selected from the group consisting of:
    (a) a nucleotide sequence encoding the amino acid sequence of SEQ ID NO:1; and
    (b) a nucleotide sequence set forth in SEQ ID NO:2.

12. A transformed plant having stably incorporated into its genome an expression cassette comprising at least one nucleotide sequence encoding a hydroperoxide lyase protein, said nucleotide sequence operably linked to a promoter that drives expression in a plant cell, wherein said nucleotide sequence is selected from the group consisting of:
    (a) a nucleotide sequence encoding the amino acid sequence of SEQ ID NO:1; and
    (b) a nucleotide sequence set forth in SEQ ID NO:2.

13. The plant of claim 12, wherein said plant is a monocot.

14. The plant of claim 13, wherein said monocot is maize, wheat, rice, barley, sorghum, or rye.

15. The plant of claim 12, wherein said plant is a dicot.

16. The plant of claim 15, wherein said dicot is soybean, canola, sunflower, alfalfa, safflower, or green pepper.

17. Seed of the plant of claim 12, wherein the seed comprises the expression cassette.

\* \* \* \* \*